US008330005B2

(12) United States Patent
Hoopes

(10) Patent No.: US 8,330,005 B2
(45) Date of Patent: Dec. 11, 2012

(54) POTATO CULTIVAR FL 2137

(75) Inventor: Robert W. Hoopes, Rhinelander, WI (US)

(73) Assignee: Frito-Lay North America, Inc., Plano, TX (US)

(*) Notice: Subject to any disclaimer, the term of this patent is extended or adjusted under 35 U.S.C. 154(b) by 704 days.

(21) Appl. No.: 12/043,621

(22) Filed: Mar. 6, 2008

(65) Prior Publication Data
US 2009/0229001 A1 Sep. 10, 2009

(51) Int. Cl.
*A01H 5/00* (2006.01)
*A01H 5/02* (2006.01)
*A01H 5/04* (2006.01)
*A01H 5/06* (2006.01)
*A01H 5/10* (2006.01)
*A01H 5/12* (2006.01)
*A01H 4/00* (2006.01)
*A01H 1/00* (2006.01)
*C12N 15/82* (2006.01)

(52) U.S. Cl. ............... 800/317.2; 800/260; 800/263; 800/265; 800/268; 800/274; 800/278; 800/279; 800/284; 800/295; 800/298; 800/300; 800/301; 800/302; 800/303

(58) Field of Classification Search ............... None
See application file for complete search history.

(56) References Cited

U.S. PATENT DOCUMENTS

| | | | |
|---|---|---|---|
| 5,304,719 A | 4/1994 | Segebart | |
| 5,367,109 A | 11/1994 | Segebart | |
| 5,523,520 A | 6/1996 | Hunsperger et al. | |
| 5,763,755 A | 6/1998 | Carlone | |
| 5,850,009 A * | 12/1998 | Kevern | 800/271 |
| 6,492,580 B1 * | 12/2002 | Hoopes | 800/317.2 |
| 6,870,082 B2 | 3/2005 | Hoopes | |

OTHER PUBLICATIONS

Poehlman, J.M. and D.A. Sleper. 1995. Breeding Field Crops. 4th ed. Iowa State University Press, Ames, Iowa, p. 473.*
Bennetzen, et al., 1992. Approaches and progress in the molecular cloning of plant disease resistance genes. In Genetic Engineering. 14:99-124.
Darnell, et al., 1990. DNA replication, repair and recombination. In Molecular Cell Biology, 2$^{nd}$ Edition, W. H. Freeman and Company, p. 478.
DeBolle, et al., 1996. Antimicrobial peptides from *Mirabilis Jalapa* and *Amaranthus caudatus* : expression, processing, localization and biological activity in transgenic tobacco. Plant Molecular Biology. 31:993-1008.
Eshed, et al., 1996. Less-than-additive epistatic interactions of quantitative trait loci in tomato. Genetics. 143:1807-1817.
Goth, et al., 1995. Relative resistance of the potato cultivar Krantz to common scab caused by *Streptomyces scabies* as determined by cluster analysis. American Potato Journal 72:505-511.
Hemmat, et al., 1998. Molecular markers for the scab resistance ($V_f$) region in apple. J. Amer. Soc. Hort. Sci. 123 (6):992-996.
Kraft, et al., 2000. Linkage disequilibrium and fingerprinting in sugar beet. Theor. Appl. Genet. 101:323-326.
Lopez, et al., 1987. Genotype x environment interactions, correlations and combining ability for six traits in potato. American Potato Journal. 64:447.
Mendiburu, et al., 1977. The significance of 2N gametes in potato breeding. Theor Appl. Genet. 49:53-61.
Michelmore, et al., 1991 Identification of markers linked to disease-resistance genes by bulked segregant analysis: a rapid method to detect markers in specific genomic regions by using segregating populations. PNAS (USA) 88:9828-9832.
Pang, et al., 1992. Expression of a gene encoding a scorpion insectotoxin peptide in yeast, bacteria and plants. Gene 116:165-172.
Poehlman, J.M. and Sleper, D.A. Breeding Field Crops, 4$^{th}$ Ed. (1995), Iowa State University Press, Ames, Iowa, p. 473.
Van Ooijen, et al., 1994. An RFLP linkage map of *Lycopersicon peruvianum*. Theor. Appl. Genet. 89:1007-1013.
Visker, et al., 2003. Can the QTL for late blight resistance on potato chromosome 5 be attributed to foliage maturity type? Theor. Appl. Genet. 106:317-325.
US PVP Database, Application No. 200800036 of Frito-Lay North America, Inc., filed Nov. 28, 2007.
US PVP Certificate No. 200200127, Granted Application of Frito-Lay North America, Inc., Jun. 5, 2008.
Canadian PBR Database, Application No. 08-6423 of Frito-Lay North America, Inc., filed Jul. 31, 2008.
Canadian PBR Database, Application No. 92-155 of Frito-Lay North America, Inc., filed Nov. 6, 1992, withdrawn Jul. 15, 1997.

* cited by examiner

*Primary Examiner* — Cathy Kingdon Worley
(74) *Attorney, Agent, or Firm* — Jondle & Associates, P.C.

(57) ABSTRACT

A potato cultivar designated FL 2137 is disclosed. The invention relates to the tubers of potato cultivar FL 2137, to the seeds of potato cultivar FL 2137, to the plants of potato FL 2137, to the plant parts of potato cultivar FL 2137 and to methods for producing a potato plant produced by crossing potato cultivar FL 2137 with itself or with another potato variety. The invention also relates to methods for producing a potato plant containing in its genetic material one or more transgenes and to the transgenic potato plants and plant parts produced by those methods. This invention also relates to potato cultivars or breeding cultivars and plant parts derived from potato variety FL 2137, to methods for producing other potato cultivars, lines or plant parts derived from potato cultivar FL 2137 and to the potato plants, varieties, and their parts derived from use of those methods. The invention further relates to hybrid potato tubers, seeds, plants and plant parts produced by crossing potato cultivar FL 2137 with another potato cultivar.

12 Claims, No Drawings

POTATO CULTIVAR FL 2137

BACKGROUND OF THE INVENTION

The present invention relates to a novel potato variety and to the tubers, plants, plant parts, tissue culture and seeds produced by that potato variety. All publications cited in this application are herein incorporated by reference.

The potato is the world's fourth most important food crop and by far the most important vegetable. Potatoes are currently grown commercially in nearly every state of the United States. Annual potato production exceeds 18 million tons in the United States and 300 million tons worldwide. The popularity of the potato derives mainly from its versatility and nutritional value. Potatoes can be used fresh, frozen or dried, or can be processed into flour, starch or alcohol. They contain complex carbohydrates and are rich in calcium, niacin and vitamin C.

To keep the potato industry growing to meet the needs of the consuming public, substantial research and development efforts are devoted to the modernization of planting and harvesting of fields and processing of potatoes, and to the development of economically advantageous potato varieties. Through crossbreeding of potatoes, researchers hope to obtain potatoes with the desirable characteristics of good processability, high solids content, high yield, resistance to diseases and pests and adaptability to various growing areas and conditions.

The U.S. acreage planted in potatoes has declined since the 1960s and 1970s, and this decline, coupled with increasing consumption, must be offset by higher useable yields. In some areas, diseases and pests damage crops despite the use of herbicides and pesticides. The problem of the golden nematode in the United States, presently endemic to portions of New York State, is one example of the destruction to susceptible potato varieties. Potato varieties with high yields, disease resistance and adaptability to new environments can eliminate many problems for the potato grower and provide more plentiful and economical products to the consumers.

For the potato chip processing industry, potatoes having high solids content, good shipping qualities and good finished chip color can increase production volumes and efficiencies and product acceptability. Potato varieties which yield low-solids tubers result in unnecessary energy usage during the frying process. Moreover, as solids content increases, the oil content of fried products decreases, which is a favorable improvement. Potato varieties in the warm southern tier of states are most in need of solids improvement overall, while those varieties grown and stored in the colder northern tier of states are most in need of the ability to recondition after cool or cold storage to increase their value for use in the potato chip industry. Reconditioning is necessary to elevate the temperature of the potatoes after cold storage and before further processing.

The research leading to potato varieties which combine the advantageous characteristics referred to above is largely empirical. This research requires large investments of time, labor, and money. The development of a potato cultivar can often take up to eight years or more from greenhouse to commercial usage. Breeding begins with careful selection of superior parents to incorporate the most important characteristics into the progeny. Since all desired traits usually do not appear with just one cross, breeding must be cumulative.

Present breeding techniques continue with the controlled pollination of parental clones. Typically, pollen is collected in gelatin capsules for later use in pollinating the female parents. Hybrid seeds are sown in greenhouses and tubers are harvested and retained from thousands of individual seedlings. The next year a single tuber from each resulting seedling is planted in the field, where extreme caution is exercised to avoid the spread of virus and diseases. From this first-year seedling crop, several "seed" tubers from each hybrid individual which survived the selection process are retained for the next year's planting. After the second year, samples are taken for density measurements and fry tests to determine the suitability of the tubers for commercial usage. Plants which have survived the selection process to this point are then planted at an expanded volume the third year for a more comprehensive series of fry tests and density determinations. At the fourth-year stage of development, surviving selections are subjected to field trials in several states to determine their adaptability to different growing conditions. Eventually, the varieties having superior qualities are transferred to other farms and the seed increased to commercial scale. Generally, by this time, eight or more years of planting, harvesting and testing have been invested in attempting to develop the new and improved potato cultivars.

Long-term, controlled-environment storage has been a feature of the northern, principal producing areas for many years. Potatoes harvested by October must be kept in good condition for up to eight months in temperatures that may drop to −30 degrees C. at times and with very low relative humidity in the outside air. Storages are well insulated, not only to prevent heat loss but also to prevent condensation on outside walls. The circulation of air at the required temperature and humidity is automatically controlled depending on the purpose for which the potatoes are being stored. Sprout inhibition is now largely carried out in storage as it has been found to be more satisfactory than the application of maleic hydrazide (MH30) in the field.

Proper testing of new plants should detect any major faults and establish the level of superiority or improvement over current varieties. In addition to showing superior performance, a new variety must be compatible with industry standards or create a new market. The introduction of a new variety will increase costs of the tuber propagator, the grower, processor and consumer for special advertising and marketing, altered tuber propagation and new product utilization. The testing preceding release of a new variety should take into consideration research and development costs as well as technical superiority of the final variety. Once the varieties that give the best performance have been identified, the tuber can be propagated indefinitely as long as the homogeneity of the variety parent is maintained.

For tuber propagated varieties, it must be feasible to produce, store and process potatoes easily and economically. Thus, there is a continuing need to develop potato cultivars which provide good processability out of storage, with minimal bruising, for manufacturers of potato chips and other potato products and to combine this characteristic with the properties of disease and pest resistance. The present invention addresses this need by providing the new variety as described herein.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

According to the invention, there is provided a new potato cultivar of the genus and species *Solanum tuberosum L.*, designated FL 2137. This invention thus relates to the tubers of potato cultivar FL 2137, to the plants of potato cultivar FL 2137 and to methods for producing a potato plant produced by crossing potato cultivar FL 2137 with itself or another potato cultivar, and the creation of variants by mutagenesis or transformation of potato cultivar FL 2137.

Thus, any such methods using the cultivar FL 2137 are part of this invention: selfing, backcrosses, hybrid production, crosses to populations, and the like. All plants produced using potato cultivar FL 2137 as at least one parent are within the scope of this invention. Advantageously, the potato cultivar could be used in crosses with other, different, potato plants to produce first generation ($F_1$) potato hybrid seeds and plants with superior characteristics.

In another aspect, the present invention provides for single or multiple gene converted plants of potato cultivar FL 2137. The transferred gene(s) may preferably be a dominant or recessive allele. Preferably, the transferred gene(s) will confer such traits as herbicide resistance, insect resistance, resistance for bacterial, fungal, or viral disease, male fertility, male sterility, enhanced nutritional quality, uniformity and increase in concentration of starch and other carbohydrates, decrease in tendency to bruise and decrease in the rate of conversion of starch to sugars. The gene may be a naturally occurring potato gene or a transgene introduced through genetic engineering techniques.

In another aspect, the present invention provides regenerable cells for use in tissue culture of potato cultivar FL 2137. The tissue culture will preferably be capable of regenerating plants having all the physiological and morphological characteristics of the foregoing soybean plant, and of regenerating plants having substantially the same genotype as the foregoing potato plant. Preferably, the regenerable cells in such tissue cultures will be embryos, protoplasts, meristematic cells, callus, pollen, leaves, anthers, cotyledons, hypocotyl, pistils, roots, root tips, flowers, seeds, petiole, tubers or stems. Still further, the present invention provides potato plants regenerated from the tissue cultures of the invention.

In addition to the exemplary aspects and embodiments described above, further aspects and embodiments will become apparent by study of the following descriptions.

Definitions

In the description and tables which follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Bacterial Ring Rot. Bacterial ring rot is a disease caused by the bacterium *Clavibacter michiganense* ssp. Bacterial ring rot derives its name from a characteristic breakdown of the vascular ring within the tuber. This ring often appears as a creamy-yellow to light-brown, cheesy rot. On the outer surface of the potato, severely diseased tubers may show slightly sunken, dry and cracked areas. Symptoms of bacterial ring rot in the vascular tissue of infected tubers can be less obvious than described above, appearing as only a broken, sporadically appearing dark line or as a continuous, yellowish discoloration.

Black spot. Black spots found in bruised tuber tissue are a result of a pigment called melanin that is produced following the injury of cells and gives tissue a brown, gray or black appearance. Melanin is formed when phenol substrates and an appropriate enzyme come in contact with each other as a result of cellular damage. The damage does not require broken cells. However, mixing of the substrate and enzyme must occur, usually when the tissue is impacted. Black spots occur primarily in the perimedullary tissue just beneath the vascular ring, but may be large enough to include a portion of the cortical tissue.

Cotyledon. A cotyledon is a type of seed leaf. The cotyledon contains the food storage tissues of the seed.

Embryo. The embryo is the small plant contained within a mature seed.

FL Solids. Percentage of solid matter contained in tubers.

$$FL\ Solids = (178.93 \times Specific\ gravity\ of\ sample) - 175.560.$$

Hypocotyl. A hypocotyl is the portion of an embryo or seedling between the cotyledons and the root. Therefore, it can be considered a transition zone between shoot and root.

Marketable Yield. Weight of all tubers harvested that are between 2 and 4 inches in diameter; Measured in cwt (hundred weight) cwt=100 pounds Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Single Gene Converted (Conversion). Single gene converted (conversion) plant refers to plants which are developed by a plant breeding technique called backcrossing wherein essentially all of the desired morphological and physiological characteristics of a variety are recovered in addition to the single gene transferred into the variety via the backcrossing technique or via genetic engineering.

Solid/Acre. Marketable yield (in pounds)×FL Solids.

Total Yield. Total weight of all harvested tubers.

Vine Maturity. Plants ability to continue to utilize carbohydrates and photosynthesize. Scale of 1 to 5. 1=dead vines 5=vines green, still flowering.

DETAILED DESCRIPTION OF THE INVENTION

A potato cultivar of the present invention, designated FL 2137, has been obtained by selectively crossbreeding parental clones through several generations. The parents of FL 2137 are FL 2006 and FL 1291. The parent FL 2006 was selected for its good solids, high yield, excellent chip color, both fresh and out of storage, and its golden flesh color. The parent FL 1291 was chosen for its high yield and common scab and bruise resistance.

Potato cultivar FL 2137 has round tubers with white flesh and shallow eyes. Potato cultivar FL 2137's outstanding attributes are its excellent chip color through late storage, its high solids, very low glycoalkaloid content, yield and tuber appearance.

Potato cultivar FL 2137 has been uniform and stable since its origin as a single plant in 2000. No variants of potato cultivar FL 2137 have been observed.

In addition to the morphological characteristics and disease and pest resistance as described above, the plants of this invention are characterized by their protein "fingerprint" patterns. The protein "fingerprint" is determined by extracting tuber proteins and separating the proteins on an electrophoretic gel under certain defined conditions. The pattern of the proteins, attributable to their differential mobilities on the electrophoretic gel, has been found to be characteristic of the particular plant involved. This pattern has thus been termed a "fingerprint." Isozyme fingerprints of all available North American potato varieties have revealed that no two varieties have the same pattern for the enzymes tested (Douches and Ludlam, 1991). The isozyme fingerprint of FL 2137 has been established as distinct from that of any other variety tested, including Atlantic, Norchip and Snowden (Douches, 2005).

Potato variety FL 2137 has the following morphologic and other characteristics (Based on data collected in Wisconsin).

TABLE 1

| VARIETY DESCRIPTION INFORMATION | |
|---|---|
| Classification: | *Solanum tuberosum* L. |
| Plant characteristics: | (Observed at beginning of bloom) |
| | Growth habit: Spreading |
| | Type: Stem (foliage opens and stems are clearly visible) |
| | Maturity: 130 days after planting at vine senescence |
| | Planting Date: Apr. 27, 2005 |
| | Regional Area: North Central (North Dakota, Wisconsin, Michigan, Minnesota and Ohio) |
| | Maturity Class: Late |
| | Market Class: Chip-processing |
| Stem Characteristics: | (Observed at early first bloom) |
| | Stem anthocyanin coloration: Strong |
| | Stem wings: Weak |
| Light Sprout Characteristics: | General shape: Conical |
| | Base, pubescence of tip: Medium |
| | Base anthocyanin coloration: Blue-violet |
| | Base intensity of anthocyanin coloration: Very Strong |
| | Tip habit: Closed |
| | Tip pubescence: Absent |
| | Tip anthocyanin coloration: Blue-violet |
| | Tip intensity of anthocyanin coloration: Very Strong |
| Leaf Characteristics: | (Observed fully developed leaves located in the middle one-third of plant): |
| | Leaf color: RHS 147A (dark green) |
| | Leaf silhouette: Open |
| | Petioles anthocyanin coloration: Strong |
| | Terminal leaflet shape: Medium ovate |
| | Terminal leaflet tip shape: Acuminate |
| | Terminal leaflet base shape: Cordate to truncate |
| | Terminal leaflet margin waviness: Weak |
| | Number of primary leaflet pairs: 5.45 |
| | Range of primary leaflet pairs: 5 to 6 |
| | Primary leaflet tip shape: Acuminate |
| | Primary leaflet size: Medium |
| | Primary leaflet shape: Medium ovate |
| | Primary leaflet base shape: Cordate |
| | Number of secondary and tertiary leaflets (average): 9 |
| | Range of secondary and tertiary leaflets: 5 to 12 |
| Inflorescence Characteristics: | Number of inflorescences/plant: 4 |
| | Range of inflorescences/plant: 1 to 8 |
| | Number of florets/inflorescence: 8.7 |
| | Range of florets/inflorescence: 4 to 16 |
| | Corolla shape: Pentagonal |
| | Corolla inner surface color: RHS N88A (blue-violet) |
| | Corolla outer surface color: RHS N88B (blue-violet, with white tips on back) |
| | Calyx anthocyanin coloration: Very strong |
| | Anther color: RHS 14A |
| | Anther shape: Narrow cone to pear-shaped cone |
| | Pollen Production: Abundant |
| | Stigma shape: Capitate |
| | Stigma color: RHS 137C |
| Tuber Characteristics: | Skin predominant color: RHS 199C (tan) |
| | Skin secondary color: RHS 83B (violet) |
| | Skin secondary color distribution: Eyes |
| | Skin texture: Smooth to rough (flaky) |
| | Tuber shape: Round |
| | Tuber thickness: Round |
| | Tuber eye depth: Shallow |
| | Tuber lateral eyes: Shallow |
| | Distribution of tuber eyes: Predominantly apical |
| | Prominence of tuber eyebrows: Slight prominence |
| | Predominant tuber flesh color: RHS 155D (white) |
| | Secondary tuber flesh color: Absent |
| | Total glycoalkaloid content: 2.65 mg/100 g of fresh tuber |

TABLE 1-continued

VARIETY DESCRIPTION INFORMATION

Disease reactions: Late blight (*Phytophthora*): Moderately susceptible
Early blight (*Alternaria*): Moderately susceptible
Common scab (*Streptomyces*): Resistant; few lessions in number and size
Powdery scab (*Spongospora*): Moderately resistant
Pink rot: Moderately susceptible
Pythium Leak: Moderately susceptible Table 2 shows differences between potato cultivar FL 2137 and potato cultivar Atlantic. Column one shows a list of characteristics and column two and three show the characteristic for FL 2137 and Atlantic, respectively.

TABLE 2

| | Potato Variety | |
|---|---|---|
| Characteristic | FL 2137 | Atlantic |
| Growth habit | Spreading | Semi erect (30-40° with ground) |
| Leaf color | RHS 147A (dark green) | RHS 147B (medium green) |
| Number of secondary and tertiary leaflet pairs | 9 | 8.6 |
| Stem anthocynanin | Strong | Weak |
| Corolla inner surface color | RHS N88A (blue-violet) | RHS N82B (purple-violet with white tips) |
| Tuber secondary skin color | Present | Absent |
| Tuber eye depth | Shallow | Intermediate - deep |
| Common scab (*Streptomyces*) | Resistant; few lesions in number and size | Moderately resistance |
| Glycoalkaloid content | 2.65 mg/100 g of fresh tuber | 6.945 mg/100 g of fresh tuber |

Further Embodiments of the Invention

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed variety or line.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed potato plants, using transformation methods as described below to incorporate transgenes into the genetic material of the potato plant(s).

Expression Vectors for Potato Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Fraley et al., *Proc. Natl. Acad. Sci.* U.S.A., 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase and aminoglycoside-3'-adenyl transferase, the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990) Hille et al., *Plant Mol. Biol.* 7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990) and Stalker et al., *Science* 242:419-423 (1988).

Selectable marker genes for plant transformation not of bacterial origin include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci.* USA 84:131 (1987), DeBlock et al., *EMBO J.* 3:1681 (1984).

In vivo methods for visualizing GUS activity that do not require destruction of plant tissue are available. Molecular Probes publication 2908, IMAGENE GREEN, p. 1-4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263: 802 (1994). GFP and mutants of GFP may be used as screenable markers.

Expression Vectors for Potato Transformation: Promoters

Genes included in expression vectors must be driven by a nucleotide sequence comprising a regulatory element, for example, a promoter. Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters that initiate transcription only in a certain tissue are referred to as "tissue-specific". A "cell-type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

A. Inducible Promoters

An inducible promoter is operably linked to a gene for expression in potato. Optionally, the inducible promoter is operably linked to a nucleotide sequence encoding a signal sequence which is operably linked to a gene for expression in potato. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Mett et al., *PNAS* 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) or Tet repressor from Tn10 (Gatz et al., *Mol. Gen. Genetics* 227: 229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci.* USA 88:0421 (1991).

B. Constitutive Promoters

A constitutive promoter is operably linked to a gene for expression in potato or the constitutive promoter is operably linked to a nucleotide sequence encoding a signal sequence which is operably linked to a gene for expression in potato.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2: 163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., EMBO J. 3:2723-2730 (1984)) and maize H3 histone (Lepetit et al., *Mol. Gen. Genetics* 231:276-285 (1992) and Atanassova et al., *Plant Journal* 2 (3): 291-300 (1992)).

The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO 96/30530.

C. Tissue-specific or Tissue-preferred Promoters

A tissue-specific promoter is operably linked to a gene for expression in potato. Optionally, the tissue-specific promoter is operably linked to a nucleotide sequence encoding a signal sequence which is operably linked to a gene for expression in potato. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., *Science* 23:476-482 (1983) and Sengupta-Gopalan et al., *Proc. Natl. Acad. Sci.* USA 82:3320-3324 (1985)); a leaf-specific and light-induced promoter such as that from cab or rubisco (Simpson et al., *EMBO J.* 4(11): 2723-2729 (1985) and Timko et al., Nature 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker et al., *Plant Mol. Biol.* 20:49 (1992); Close, P. S., Master's Thesis, Iowa State University (1993); Knox, C., et al., *Plant Mol. Biol.* 9:3-17 (1987); Lerner et al., *Plant Physiol.* 91:124-129 (1989); Frontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499-509 (1984); Steifel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is a potato plant. In another preferred embodiment, the biomass of interest is seed or tubers. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology *CRC Press*, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene(s) to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al. *Cell* 78:1089 (1994) (*Arabidopsis* RSP2 gene for resistance to *Pseudomonas syringae*).

B. A gene conferring resistance to a pest, such as soybean cyst nematode. See e.g., PCT Application WO 96/30517; PCT Application WO 93/19181.

C. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, Van Damme et al., *Plant Molec. Biol.* 24:25 (1994), who disclose the nucleotide sequences of several *Clivia miniata* mannose-binding lectin genes.

E. A vitamin-binding protein such as avidin. See PCT application US 93/06487 which teaches the use of avidin and avidin homologs as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid or juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., *Gene* 116:165 (1992), for disclosure of heterologous expression in plants of a gene coding for a scorpion insectotoxic peptide.

J. An enzyme responsible for a hyperaccumulation of a monoterpene, a sesquiterpene, a steroid, hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 (Scott et al.), which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant*

*Molec. Biol.* 21:673 (1993), who provide the nucleotide sequence of the parsley ubi4-2 polyubiquitin gene.

L. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

M. A hydrophobic moment peptide. See PCT application WO 95/16776, which discloses peptide derivatives of Tachyplesin which inhibit fungal plant pathogens, and PCT application WO 95/18855 which teaches synthetic antimicrobial peptides that confer disease resistance.

N. A membrane permease, a channel former or a channel blocker. For example, see the disclosure of Jaynes et al., *Plant Sci* 89:43 (1993), of heterologous expression of a cecropin-β lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus and tobacco mosaic virus.

P. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Tavladoraki et al., *Nature* 366:469 (1993), who show that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

S. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

T. Genes involved in the Systemic Acquired Resistance (SAR) Response and/or the pathogenesis-related genes. Briggs, S. *Current Biology,* 5(2) (1995).

U. Antifungal genes. See Cornelissen and Melchers, Plant Physiol., 101:709-712 (1993); Parijs et al., *Planta* 183:258-264 (1991) and Bushnell et al., *Can. J. of Plant Path.* 20(2): 137-149 (1998).

V. Genes that confer resistance to *Phytophthora* blight, such as the R1, R2, R3, R4 and other resistance genes. See, Naess, S. K., et. al., (2000) Resistance to late blight in *Solanum bulbocastanum* is mapped to chromosome 8. *Theor. Appl. Genet.* 101: 697-704 and Li, X., et. al., (1998) Autotetraploids and genetic mapping using common AFLP markers: the R2 allele conferring resistance to *Phytophthora infestans* mapped on potato chromosome 4. *Theor. Appl. Genet.* 96: 1121-1128.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance impaired by mutant 5-enolpyruvlshikimate-3-phosphate synthase (EPSP) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *Bio/Technology* 7:61 (1989) describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop are the Acc1-S1, Acc1-S2, and Acc2-S3 genes described by Marshall et al., *Theor. Appl. Genet.* 83:435 (1992).

C. An herbicide that inhibits photosynthesis, such as a triazine (psbA and gs+ genes) or a benzonitrile (nitrilase gene). Przibila et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC Accession Nos. 53435, 67441 and 67442. Cloning and expression of DNA coding for a glutathione S-transferase is described by Hayes et al., *Biochem. J.* 285:173 (1992).

D. Acetohydroxy acid synthase, which has been found to make plants that express this enzyme resistant to multiple types of herbicides, has been introduced into a variety of plants. See Hattori et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota et al., Plant Physiol., 106:17, 1994), genes for glutathione reductase and superoxide dismutase (Aono et al., *Plant Cell Physiol.* 36:1687, 1995), and genes for various phosphotransferases (Datta et al., *Plant Mol. Biol.* 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

3. Genes that Confer or Contribute to a Value-Added Trait, such as:

A. Modified fatty acid metabolism, for example, by transforming a plant with an antisense gene of stearyl-ACP desaturase to increase stearic acid content of the plant. See Knultzon et al., *Proc. Natl. Acad. Sci.* USA 89:2625 (1992).

B. Decreased phytate content—1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an Aspergillus niger phytase gene. 2) A gene could be introduced that reduced phytate content. In maize, for example, this could be accomplished by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteriol.* 170:810 (1988) (nucleotide sequence of *Streptococcus mutans* fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus lichenifonnis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

D. Elevated oleic acid via FAD-2 gene modification and/or decreased linolenic acid via FAD-3 gene modification. See U.S. Pat. Nos. 6,063,947; 6,323,392; and international publication WO 93/11245.

4. Genes that Control Male Sterility

A. Introduction of a deacetylase gene under the control of a tapetum-specific promoter and with the application of the chemical N—Ac—PPT. See international publication WO 01/29237.

B. Introduction of various stamen-specific promoters. See international publications WO 92/13956 and WO 92/13957.

C. Introduction of the barnase and the barstar genes. See Paul et al., Plant Mol. Biol. 19:611-622, 1992).

Methods for Potato Transformation

Numerous methods for plant transformation have been developed including biological and physical plant transformation protocols. See, for example, Miki et al., "Procedures for Introducing Foreign DNA into Plants" in Methods in Plant Molecular *Biology and Biotechnology*, Glick, B. R. and Thompson, J. E. Eds. (*CRC Press, Inc.* Boca Raton, 1993) pages 67-88. In addition, expression vectors and in-vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (*CRC Press, Inc.,* Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes,* respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra and Moloney et al., *Plant Cell Reports* 8:238 (1989). See also, U.S. Pat. No. 5,563,055 (Townsend and Thomas), issued Oct. 8, 1996.

B. Direct Gene Transfer—Several methods of plant transformation collectively referred to as direct gene transfer have been developed as an alternative to *Agrobacterium*-mediated transformation. A generally applicable method of plant surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987); Sanford, J. C., *Trends Biotech.* 6:299 (1988); Klein et al., *Bio/Tech.* 6:559-563 (1988); Sanford, J. C. *Physiol Plant* 7:206 (1990); Klein et al., *Biotechnology* 10:268 (1992). See also U.S. Pat. No. 5,015,580 (Christou, et al.), issued May 14, 1991 and U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.,* 4:2731 (1985); Christou et al., *Proc Natl. Acad. Sci.* USA 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994).

Following transformation of potato target tissues, expression of the above-described selectable marker genes allows for preferential selection of transformed cells, tissues and/or plants, using regeneration and selection methods well known in the art.

The foregoing methods for transformation would typically be used for producing a transgenic variety. The transgenic variety could then be crossed with another (non-transformed or transformed) variety in order to produce a new transgenic variety. Alternatively, a genetic trait that has been engineered into a particular potato line using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple X by Y cross or the process of backcrossing depending on the context.

Persons of ordinary skill in the art will recognize that when the term potato plant is used in the context of the present invention, this also includes derivative varieties that retain the essential distinguishing characteristics of FL 2137, such as a Single Gene Converted plant of that variety or a transgenic derivative having one or more value-added genes incorporated therein (such as herbicide or pest resistance). Backcrossing methods can be used with the present invention to improve or introduce a characteristic into the variety. The term "backcrossing" as used herein refers to the repeated crossing 1, 2, 3, 4, 5, 6, 7, 8, 9 or more times of a hybrid progeny back to the recurrent parents. The parental potato plant which contributes the gene for the desired characteristic is termed the nonrecurrent or donor parent. This terminology refers to the fact that the nonrecurrent parent is used one time in the backcross protocol and therefore does not recur. The parental potato plant to which the gene or genes from the nonrecurrent parent are transferred is known as the recurrent parent as it is used for several rounds in the backcrossing protocol. In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a potato plant is obtained wherein essentially all of the desired morphological and physiological characteristics of the recurrent parent are recovered in the converted plant, in addition to the single gene transferred from the nonrecurrent parent, as determined at the 5% significance level when grown under the same environmental conditions.

The selection of a suitable recurrent parent is an important step for a successful backcrossing procedure. The goal of a backcross protocol is to alter or substitute a single trait or characteristic in the original variety. To accomplish this, a single gene of the recurrent variety is modified, substituted or supplemented with the desired gene from the nonrecurrent parent, while retaining essentially all of the rest of the desired genes, and therefore the desired physiological and morphological constitution of the original variety, as determined at the 5% significance level when grown under the same environmental conditions. The choice of the particular nonrecurrent parent will depend on the purpose of the backcross. One of the major purposes is to add some commercially desirable, agronomically important trait to the plant. The exact backcrossing protocol will depend on the characteristic or trait being altered or added to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred.

Likewise, transgenes can be introduced into the plant using any of a variety of established recombinant methods well-known to persons skilled in the art, such as: Gressel, 1985, Biotechnologically Conferring Herbicide Resistance in Crops: The Present Realities, In Molecular Form and Function of the Plant Genome, L. van Vloten-Doting, (ed.), Plenum Press, New York; Huttner, S. L., et al., 1992, Revising Oversight of Genetically Modified Plants, *Bio/Technology*; Klee, H., et al., 1989, Plant Gene Vectors and Genetic Transformation: Plant Transformation Systems Based on the use of *Agrobacterium tumefaciens, Cell Culture and Somatic Cell Genetics of Plants*; Koncz, C., et al., 1986, The Promoter of T$_L$-DNA Gene 5 Controls the Tissue-Specific Expression of Chimeric Genes Carried by a Novel Type of *Agrobacterium* Binary Vector; *Molecular and General Genetics*; Lawson, C., et al., 1990, Engineering Resistance to Mixed Virus Infection in a Commercial Potato Cultivar: Resistance to Potato Virus X and Potato Virus Y in Transgenic Russet Burbank, *Bio/Technology*; Mitsky, T. A., et al., 1996, Plants Resistant to Infection by PLRV. U.S. Pat. No. 5,510,253; Newell, C. A., et al., 1991, *Agrobacterium*-Mediated Transformation of *Solanum tuberosum* L. Cv. Russet Burbank, *Plant Cell Reports*; Perlak, F. J., et al., 1993, Genetically Improved Potatoes: Protection from Damage by Colorado Potato Beetles, *Plant Molecular Biology*; all of which are specifically incorporated herein by reference.

Many single gene traits have been identified that are not regularly selected for in the development of a new variety but that can be improved by backcrossing and genetic engineering techniques. Single gene traits may or may not be transgenic, examples of these traits include but are not limited to: herbicide resistance; resistance to bacterial, fungal or viral disease; insect resistance; uniformity or increase in concentration of starch and other carbohydrates; enhanced nutritional quality; decrease in tendency of tuber to bruise; and decrease in the rate of starch conversion to sugars. These genes are generally inherited through the nucleus. Several of these single gene traits are described in U.S. Pat. Nos. 5,500,365, 5,387,756, 5,789,657, 5,503,999, 5,589,612, 5,510,253, 5,304,730, 5,382,429, 5,503,999, 5,648,249, 5,312,912, 5,498,533, 5,276,268, 4,900,676, 5,633,434 and 4,970,168.

DEPOSIT INFORMATION

A tuber deposit of the FRITO-LAY NORTH AMERICA, INC. proprietary POTATO CULTIVAR FL 2137 disclosed above and recited in the appended claims has been made with the American Type Culture Collection (ATCC), 10801 University Boulevard, Manassas, Va. 20110. The date of deposit was Jun. 27, 2012. The deposit of 25 vials of microtubers was taken from the same deposit maintained by FRITO-LAY NORTH AMERICA, INC. since prior to the filing date of this application. All restrictions will be irrevocably removed upon granting of a patent, and the deposit is intended to meet all of the requirements of 37 C.F.R. §§1.801-1.809. The ATCC Accession Number is PTA-13018. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their rule spirit and scope.

What is claimed is:

1. A potato tuber, or a part of a tuber, of potato cultivar FL 2137, wherein a representative sample of said tuber was deposited under ATCC Accession No. PTA-13018.

2. A potato plant, or a part thereof, produced by growing the tuber, or a part of the tuber, of claim 1.

3. A potato plant having all of the physiological and morphological characteristics of the plant of claim 2.

4. A tissue culture of cells produced from the plant of claim 2, wherein said cells of the tissue culture are produced from a plant part selected from the group consisting of leaf, pollen, embryo, cotyledon, hypocotyl, meristematic cell, root, root tip, pistil, anther, flowers, stem and tuber.

5. A potato plant regenerated from the tissue culture of claim 4, wherein said plant has all of the physiological and morphological characteristics of the potato cultivar FL 2137.

6. A method for producing a hybrid potato seed comprising crossing the plant of claim 2 with a different potato plant and harvesting the resultant hybrid potato seed.

7. A method for producing a potato plant that contains in its genetic material one or more transgenes, comprising crossing the potato plant of claim 2 with either a second plant of another potato cultivar which contains a transgene or a transformed potato plant of potato cultivar FL 2137, so that the genetic material of the progeny that result from the cross contains the transgene(s) operably linked to a regulatory element.

8. A method of introducing a desired trait into potato cultivar FL 2137 wherein the method comprises:
   a. crossing an FL 2137 plant, wherein a representative sample of tubers was deposited under ATCC Accession No. PTA-13018, with a plant of another potato cultivar that comprises a desired trait to produce progeny plants wherein the desired trait is selected from the group consisting of male sterility, herbicide resistance, insect resistance, modified fatty acid metabolism, modified carbohydrate metabolism and resistance to bacterial disease, fungal disease or viral disease;
   b. selecting one or more progeny plants that have the desired trait;
   c. backcrossing the selected progeny plants with FL 2137 plants to produce backcross progeny plants;
   d. selecting for backcross progeny plants that have the desired trait; and
   e. repeating steps (c) and (d) three or more times in succession to produce selected fourth or higher backcross progeny plants that comprise the desired trait and all of the physiological and morphological characteristics of potato cultivar FL 2137 listed in Table 1.

9. A potato plant produced by the method of claim 8, wherein the plant has the desired trait and all of the physiological and morphological characteristics of potato cultivar FL 2137 listed in Table 1.

10. The potato plant of claim 9, wherein the desired trait is herbicide resistance and the resistance is conferred to an herbicide selected from the group consisting of imidazolinone, sulfonylurea, glyphosate, glufosinate, L-phosphinothricin, triazine and benzonitrile.

11. The potato plant of claim 9, wherein the desired trait is insect resistance and the insect resistance is conferred by a transgene encoding a *Bacillus thuringiensis* endotoxin.

12. The potato plant of claim 9, wherein the desired trait is modified fatty acid metabolism or modified carbohydrate metabolism and said desired trait is conferred by a nucleic acid encoding a protein selected from the group consisting of fructosyltransferase, levansucrase, α-amylase, invertase and starch branching enzyme or DNA encoding an antisense of stearyl-ACP desaturase.

* * * * *